(12) United States Patent
Al-Shemmeri

(10) Patent No.: US 8,722,109 B1
(45) Date of Patent: May 13, 2014

(54) COMPOSITION COMPRISING PLANT EXTRACTS AND ESSENTIAL OILS

(71) Applicant: Abdul-Wahab Fahad Al-Shemmeri, Firdous (KW)

(72) Inventor: Abdul-Wahab Fahad Al-Shemmeri, Firdous (KW)

( * ) Notice: Subject to any disclaimer, the term of this patent is extended or adjusted under 35 U.S.C. 154(b) by 0 days.

(21) Appl. No.: 13/797,996

(22) Filed: Mar. 12, 2013

(51) Int. Cl.
  *A61K 36/00* (2006.01)
(52) U.S. Cl.
  USPC .......................................................... 424/725
(58) Field of Classification Search
  USPC .................................................. 424/725, 780
  See application file for complete search history.

(56) References Cited

U.S. PATENT DOCUMENTS

| | | | |
|---|---|---|---|
| 5,595,756 A * | 1/1997 | Bally et al. | 424/450 |
| 8,377,473 B2 * | 2/2013 | Liu et al. | 424/468 |
| 2002/0173470 A1 | 11/2002 | Flescher et al. | |
| 2005/0288239 A1 | 12/2005 | Adrian et al. | |
| 2007/0065394 A1 * | 3/2007 | Pinney | 424/74 |
| 2007/0248693 A1 | 10/2007 | Mazzio et al. | |
| 2010/0086647 A1 | 4/2010 | Kristiansen | |
| 2011/0300227 A1 | 12/2011 | Danhof | |

FOREIGN PATENT DOCUMENTS

| | | |
|---|---|---|
| CN | 101862395 A | 10/2010 |
| CN | 102114097 A | 7/2011 |
| FR | 2 502 008 | 9/1982 |
| JP | 2006-36694 | 2/2006 |

OTHER PUBLICATIONS

Gura, T .: Systems for Identifying New Drugs Are Often Faulty; Science, vol. 278, Nov. 7, 1997, pp. 1041-1042.*
Tassone et al.: Novel Therapeutic Approaches Based on the Targeting of Microenvironment-Derived Survival Pathways in Human Cancer: Experimental Models and Translational Issues; Current Pharmaceutical Design, 2007, 13, pp. 487-496.*
Amin et al., "Merits of anti-cancer plants from the Arabian Gulf region", *Cancer Therapy*, vol. 5, 55-66, 2007.

* cited by examiner

*Primary Examiner* — Patricia Leith
(74) *Attorney, Agent, or Firm* — Richard C Litman

(57) ABSTRACT

The composition for treating tumors is a natural tumor treatment made from plant extracts, animal secretions and essential oils. The composition includes a solid mixture which is taken with a liquid mixture. The solid mixture is a mixture of *Dorema ammoniacum*, castoreum, myrrh, *Cistus creticus*, *Asarum europaeum*, cucumber seed, Egyptian cucumber seed, pumpkin seed, watermelon seed, cantaloupe seed, psyllium husk, *Astragalus tragacanthus*, mastic, and lump sugar. Each of these solid ingredients is ground separately and then purified through sifting, draining and smoothing. Once ground and purified, the solid powders are mixed together into a homogenous mixture. These solids are delivered to the patient in pill, capsule, powder, solution or serum injection form. Approximately 12 grams of the solid mixture is taken with approximately 250 mL of a liquid mixture of the essential oils of *Borago officinalis*, fennel, *Trachyspermum ammi*, and *Cichorium*.

7 Claims, No Drawings

COMPOSITION COMPRISING PLANT EXTRACTS AND ESSENTIAL OILS

BACKGROUND OF THE INVENTION

1. Field of the Invention

The present invention relates to the treatment of cancer and cancerous tumors, and particularly to a natural tumor treatment made from plant extracts, animal secretions, and essential oils.

2. Description of the Related Art

The treatment of cancer and cancerous tumors commonly consists of surgery, chemotherapy, radiation therapy, immunotherapy, monoclonal antibody therapy, and combinations thereof. Each of these treatment methods has severe side effects on the patient, ranging from discomfort to potential damage to other systems in the body. Radiation therapy, for example, may damage surrounding organs and tissue through radiation exposure. Chemotherapy is well known for causing severe symptoms in patients, including hair loss, nausea, weight loss, fever, dizziness and immune suppression, among others. Immunotherapy and monoclonal antibody therapy are still somewhat experimental techniques having little data regarding future consequences of the treatment, and surgery always has risks for the patient. Thus, it would be desirable to provide a treatment for cancer and cancerous tumors that is natural, non-invasive, and which minimizes any potential side effects or risks.

Thus, a composition and method for treating tumors solving the aforementioned problems is desired.

SUMMARY OF THE INVENTION

The composition for treating tumors is a natural tumor treatment made from plant extracts, animal secretions, and essential oils. The composition includes a solid mixture, which is taken with a liquid mixture. The solid mixture is a mixture of *Dorema ammonlacum*, castoreum, myrrh, *Cistus creticus*, *Asarum europaeum*, cucumber seed, Egyptian cucumber seed, pumpkin seed, watermelon seed, cantaloupe seed, psyllium husk, *Astragalus tragacanthus*, mastic, and lump sugar. For patients with diabetes, the sugar may be removed from the solid mixture. Each of these solid ingredients is ground separately and then purified through sifting, draining and smoothing. Once ground and purified, the solid powders are mixed together into a homogenous mixture. These solids are delivered to the patient in pill, capsule, powder, solution or serum injection form. About 12 grams of the solid mixture is taken with about 250 mL of a liquid mixture of the essential oils of *Borago officinalis*, fennel, *Trachyspermum ammi*, and *Cichorium*.

These and other features of the present invention will become readily apparent upon further review of the following specification and drawings.

DETAILED DESCRIPTION OF THE PREFERRED EMBODIMENTS

The composition for treating tumors is a natural tumor treatment made from plant extracts, animal secretions, and essential oils. The composition is a mixture of *Dorema ammoniacum*, castoreum (an exudate from the castor sacs of the mature North American Beaver), myrrh, *Cistus creticus*, *Asarum europaeum* (commonly known as "Asarabacca", "European Wild Ginger", "Hazelwort", and "Wild Spikenard"), cucumber (*Cucumis sativus*) seed, Egyptian cucumber (*Cucumis chate*) seed, pumpkin seed, watermelon seed, cantaloupe seed, psyllium (also referred to as "ispaghula") husk, *Astragalus tragacanthus* (commonly known as "goat's-thorn"), mastic (the resin of *Pistacia lentiscus*, also referred to as "Arabic gum"), and lump sugar. For patients with diabetes, the sugar may be removed from the solid mixture. Exemplary quantities of each ingredient for the above composition are: 30 grams of *Dorema ammoniacum*, 30 grams of castoreum, 30 grams of myrrh, 30 grams of *Cistus creticus*, 30 grams of *Asarum europaeum*, 30 grams of cucumber seed, 30 grams of Egyptian cucumber seed, 30 grams of pumpkin seed, 30 grams of watermelon seed, 30 grams of cantaloupe seed, 30 grams of psyllium husk, 50 grams of *Astragalus tragacanthus*, 50 grams of mastic, and 200 grams of lump sugar. The total solids for these exemplary quantities have a weight of 630 grams.

Each of these solid ingredients is ground separately and then purified through sifting, draining and smoothing. Once ground and purified, the solid powders are mixed together into a homogenous mixture. These solids are delivered to the patient in pill, capsule, powder, solution or serum injection form, and are taken with 250 mL of the essential oils of *Borago officinalis* (also referred to as "Borage" or the "starflower"), fennel, *Trachyspermum ammi* (commonly known as Ajwain-Carum Copticum, "ajowan" or "ajwain", "bishop's weed", "ajowan caraway", "carom seeds", or "thymol seeds"), and *Cichorium*. These essential oils are selected due to their ability to open blockages in veins and arteries, along with strengthening of the heart and their ability to aid the body in expelling wastes and toxins.

In order to treat tumors, the patient is delivered a dose of 12 grams of the solid mixture twice daily, preferably in the morning and before dusk. It should be understood that the dosage and treatment frequency may be varied, depending upon the nature of the tumor and tumor growth. As noted above, the solid mixture is delivered to the patient in pill, capsule, powder, solution or serum injection form. Along with the solid mixture, the patient also drinks 250 mL of a liquid mixture of the essential oils of *Borago officinalis*, fennel, *Trachyspermum ammi* and *Cichorium*. The essential oils may be extracted by any suitable method, such as the well-known methods of distillation, including steam distillation, expression, boiling, solvent extraction or the like.

The composition and treatment method have been effectively applied to patients with intestinal tumors, pancreatic tumors and liver tumors. The composition has been found to effectively fight and destroy cancerous cells, dissolve tumors, and expel the resultant waste through diuresis and softening. The effects of the composition do not need to be aided by additional chemotherapy or amputation.

It is to be understood that the present invention is not limited to the embodiments described above, but encompasses any and all embodiments within the scope of the following claims.

I claim:

1. A composition, comprising:
    a solid mixture having ground *Dorema ammoniacum*, castoreum, ground myrrh, ground *Cistus creticus*, ground *Asarum europaeum*, ground cucumber seed, ground Egyptian cucumber seed, ground pumpkin seed, ground watermelon seed, ground cantaloupe seed, ground psyllium husk, ground *Astragalus tragacanthus*, and ground mastic; and
    a liquid mixture having essential oils of *Borago officinalis*, fennel, *Trachyspermum ammi*, and *Cichorium*.

2. The composition as recited in claim 1, wherein each of the ground *Dorema ammoniacum*, castoreum, ground myrrh, ground *Cistus creticus*, ground *Asarum europaeum*, ground cucumber seed, ground Egyptian cucumber seed, ground pumpkin seed, ground watermelon seed, ground cantaloupe seed, and ground psyllium husk comprises about 4.8 wt % of the solid mixture.

3. The composition as recited in claim 2, wherein the ground *Astragalus tragacanthus* comprises about 7.9 wt % of the solid mixture.

4. The composition according to claim 3, wherein the solid mixture further comprises sugar.

5. The composition of claim 1, wherein the composition comprises:
- 30 grams of ground *Dorema ammoniacum*,
- 30 grams of castoreum,
- 30 grams of ground myrrh,
- 30 grams of ground *Cistus creticus*,
- 30 grams of ground *Asarum europaeum*,
- 30 grams of ground cucumber seed,
- 30 grams of ground Egyptian cucumber seed,
- 30 grams of ground pumpkin seed,
- 30 grams of ground watermelon seed,
- 30 grams of ground cantaloupe seed,
- 30 grams of ground psyllium husk,
- 50 grams of ground *Astragalus tragacanthus* and
- 50 grams of ground mastic.

6. The composition of claim 4, wherein the composition comprises 200 grams of sugar.

7. The composition of claim 4 comprising 250 ml of the liquid mixture.

* * * * *